United States Patent
Johnsen

(10) Patent No.: US 10,449,082 B2
(45) Date of Patent: Oct. 22, 2019

(54) MOLDABLE ADHESIVE WAFERS

(71) Applicant: ConvaTec Technologies Inc., Las Vegas, NV (US)

(72) Inventor: Kenneth Johnsen, Piscataway, NJ (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 650 days.

(21) Appl. No.: 14/907,166

(22) PCT Filed: May 23, 2014

(86) PCT No.: PCT/US2014/039432
§ 371 (c)(1),
(2) Date: Jan. 22, 2016

(87) PCT Pub. No.: WO2015/012953
PCT Pub. Date: Jan. 29, 2015

(65) Prior Publication Data
US 2016/0151197 A1 Jun. 2, 2016

Related U.S. Application Data

(60) Provisional application No. 61/857,647, filed on Jul. 23, 2013.

(51) Int. Cl.
*A61F 5/443* (2006.01)
*A61F 5/448* (2006.01)
(Continued)

(52) U.S. Cl.
CPC .............. *A61F 5/448* (2013.01); *A61F 5/443* (2013.01); *A61F 5/445* (2013.01); *A61F 13/0246* (2013.01); *A61L 24/001* (2013.01)

(58) Field of Classification Search
CPC combination set(s) only.
See application file for complete search history.

(56) References Cited

U.S. PATENT DOCUMENTS 2,796,063 A 6/1975 Smelser
3,948,256 A 4/1976 Schneider
(Continued)

FOREIGN PATENT DOCUMENTS

AU 2008237157 A1 10/2008
CN 1289257 A 3/2001
(Continued)

OTHER PUBLICATIONS

Chinese Patent Application No. 201510092347.8 First Office Action dated May 17, 2016.
(Continued)

*Primary Examiner* — Tatyana Zalukaeva
*Assistant Examiner* — Guy K Townsend
(74) *Attorney, Agent, or Firm* — Wilson Sonsini Goodrich & Rosati

(57) ABSTRACT

Disclosed herein are methods and devices for coupling and securing a medical device appliance. In particular, one piece moldable adhesive structures are disclosed which allow customization of an attachment wafer to the size and shape of, for example, a stoma, while allowing flexibility and security for attaching a medical device, such as an ostomy pouch or other device to the subject.

15 Claims, 4 Drawing Sheets

(51) Int. Cl.
*A61F 5/445* (2006.01)
*A61L 24/00* (2006.01)
*A61F 13/02* (2006.01)

(56) References Cited

U.S. PATENT DOCUMENTS

| | | | |
|---|---|---|---|
| 4,204,540 A | 5/1980 | Chen et al. | |
| 4,211,224 A | 7/1980 | Kubach et al. | |
| 4,294,252 A | 10/1981 | Einset | |
| 4,359,051 A | 11/1982 | Oczkowski | |
| 4,367,732 A * | 1/1983 | Poulsen | A61L 24/0094 602/56 |
| 4,534,768 A | 8/1985 | Osburn et al. | |
| 4,551,490 A | 11/1985 | Doyle et al. | |
| 4,701,169 A | 10/1987 | Steer | |
| 5,364,379 A * | 11/1994 | Ozenne | A61F 5/448 604/342 |
| 5,545,154 A | 8/1996 | Oberholtzer | |
| 5,549,588 A | 8/1996 | Johnsen | |
| 5,865,819 A | 2/1999 | Cisko, Jr. et al. | |
| 5,976,118 A | 11/1999 | Steer | |
| 6,071,268 A | 6/2000 | Wagner | |
| 6,106,507 A | 8/2000 | Botten et al. | |
| 6,165,159 A | 12/2000 | Blanton | |
| 6,312,415 B1 * | 11/2001 | Nielsen | A61F 5/443 604/327 |
| 6,332,879 B1 * | 12/2001 | Nielsen | A61F 5/448 604/344 |
| 6,537,261 B1 | 3/2003 | Steer et al. | |
| 6,589,222 B1 * | 7/2003 | Olsen | A61F 5/443 604/336 |
| 6,626,878 B1 * | 9/2003 | Leisner | A61F 5/443 604/332 |
| 6,659,988 B1 | 12/2003 | Steer et al. | |
| 6,689,111 B2 | 2/2004 | Mulhauser et al. | |
| 6,709,421 B1 | 3/2004 | Falconer | |
| 6,746,765 B1 | 6/2004 | Fattman | |
| 6,764,474 B2 | 7/2004 | Nielsen et al. | |
| 6,840,924 B2 | 1/2005 | Buglino et al. | |
| 6,929,627 B2 | 8/2005 | Mahoney | |
| 7,090,664 B2 | 8/2006 | Holter | |
| 7,160,275 B2 | 1/2007 | Falconer | |
| 7,214,217 B2 | 5/2007 | Pedersen et al. | |
| 7,259,190 B2 | 8/2007 | Lykke | |
| 7,367,965 B2 | 5/2008 | Poulsen et al. | |
| 7,422,578 B2 | 9/2008 | Shan et al. | |
| 7,517,339 B2 | 4/2009 | Pedersen et al. | |
| 8,343,121 B2 * | 1/2013 | Cramer | A61F 5/445 604/334 |
| 8,460,259 B2 * | 6/2013 | Tsai | A61F 5/448 604/335 |
| 8,708,987 B2 | 4/2014 | Cramer et al. | |
| 9,498,372 B2 | 11/2016 | Fattman et al. | |
| 2002/0193724 A1 | 12/2002 | Stebbings et al. | |
| 2003/0004477 A1 * | 1/2003 | Nielsen | A61F 5/448 604/336 |
| 2003/0100870 A1 | 5/2003 | Villefrance | |
| 2003/0187393 A1 | 10/2003 | Cline | |
| 2004/0006320 A1 * | 1/2004 | Buglino | A61F 5/443 604/344 |
| 2004/0059306 A1 | 3/2004 | Tsai et al. | |
| 2004/0065232 A1 | 4/2004 | Lykke | |
| 2004/0102744 A1 | 5/2004 | Fattman | |
| 2004/0184876 A1 | 9/2004 | Hessel et al. | |
| 2004/0193122 A1 | 9/2004 | Cline et al. | |
| 2005/0015065 A1 | 1/2005 | Falconer | |
| 2005/0054997 A1 | 3/2005 | Buglino et al. | |
| 2005/0065486 A1 | 3/2005 | Fattman | |
| 2005/0075616 A1 | 4/2005 | Holter | |
| 2005/0085779 A1 | 4/2005 | Poulsen et al. | |
| 2005/0096611 A1 | 5/2005 | Stoyer et al. | |
| 2005/0113770 A1 | 5/2005 | Pedersen et al. | |
| 2005/0282977 A1 | 12/2005 | Stempel et al. | |
| 2006/0154145 A1 | 7/2006 | Lee | |
| 2006/0184145 A1 * | 8/2006 | Ciok | A61F 5/443 604/338 |
| 2006/0200101 A1 | 9/2006 | Mullejans et al. | |
| 2006/0206069 A1 | 9/2006 | Cline | |
| 2007/0005032 A1 | 1/2007 | Shan et al. | |
| 2007/0005033 A1 | 1/2007 | Ciok et al. | |
| 2007/0027434 A1 | 2/2007 | Pedersen et al. | |
| 2007/0088300 A1 | 4/2007 | Cline et al. | |
| 2007/0123832 A1 | 5/2007 | Cline et al. | |
| 2007/0185464 A1 | 8/2007 | Fattman et al. | |
| 2007/0191794 A1 | 8/2007 | Cline et al. | |
| 2007/0213832 A1 | 9/2007 | Wen | |
| 2007/0255240 A1 | 11/2007 | Ciok | |
| 2008/0145682 A1 * | 6/2008 | Rasmussen | B23K 26/18 428/523 |
| 2008/0269698 A1 | 10/2008 | Alexander et al. | |
| 2009/0148661 A1 | 6/2009 | Stroebech et al. | |
| 2009/0149567 A1 | 6/2009 | Lam et al. | |
| 2009/0157140 A1 | 6/2009 | Martino et al. | |
| 2009/0171258 A1 * | 7/2009 | Stroebeck | A61L 15/58 602/54 |
| 2009/0216169 A1 * | 8/2009 | Hansen | A61F 15/001 602/48 |
| 2009/0306571 A1 | 12/2009 | Lam et al. | |
| 2009/0312685 A1 * | 12/2009 | Olsen | A61F 5/443 602/54 |
| 2010/0016820 A1 | 1/2010 | Lam et al. | |
| 2010/0113999 A1 | 5/2010 | Lam et al. | |
| 2010/0114045 A1 * | 5/2010 | Cramer | A61F 5/445 604/338 |
| 2010/0121291 A1 | 5/2010 | Davies et al. | |
| 2010/0191201 A1 | 7/2010 | Bach et al. | |
| 2010/0191204 A1 | 7/2010 | Bach et al. | |
| 2010/0198176 A1 * | 8/2010 | Stroebech | A61F 5/443 604/344 |
| 2010/0204664 A1 | 8/2010 | Bach et al. | |
| 2010/0204665 A1 * | 8/2010 | Stroebech | A61F 5/443 604/344 |
| 2010/0241092 A1 | 9/2010 | Nguyen-Demary et al. | |
| 2010/0324511 A1 * | 12/2010 | Dove | A61F 5/443 604/342 |
| 2011/0040269 A1 | 2/2011 | Cline | |
| 2011/0125115 A1 | 5/2011 | Anders et al. | |
| 2011/0213321 A1 | 9/2011 | Fattman et al. | |
| 2011/0213322 A1 * | 9/2011 | Cramer | A61F 5/443 604/344 |
| 2011/0238024 A1 | 9/2011 | Smith et al. | |
| 2012/0041404 A1 * | 2/2012 | Bach | A61F 5/443 604/344 |
| 2012/0179124 A1 | 7/2012 | Nguyen-Demary et al. | |
| 2013/0226116 A1 * | 8/2013 | Edvardsen | A61F 5/445 604/338 |
| 2015/0359656 A1 * | 12/2015 | Hansen | A61F 5/443 604/344 |
| 2016/0143768 A1 * | 5/2016 | Stroebech | A61L 24/06 604/344 |
| 2017/0020713 A1 | 1/2017 | Fattman et al. | |

FOREIGN PATENT DOCUMENTS

| | | |
|---|---|---|
| CN | 1326333 A | 12/2001 |
| CN | 1878519 A | 12/2006 |
| CN | 105555244 A | 5/2016 |
| EP | 0598625 A1 | 5/1994 |
| EP | 0686381 A1 | 12/1995 |
| EP | 0853933 A1 | 7/1998 |
| EP | 2358314 A1 | 8/2011 |
| EP | 3024424 A1 | 6/2016 |
| GB | 2273049 A | 6/1994 |
| JP | S57168659 A | 10/1982 |
| JP | H0625802 A | 7/1994 |
| JP | 2005131400 A | 5/2005 |
| JP | 2007505664 A | 3/2007 |
| JP | 2016525412 A | 8/2016 |
| WO | WO-9853771 A1 | 12/1998 |
| WO | WO-03026541 A1 | 4/2003 |
| WO | WO-2004062536 A1 | 7/2004 |
| WO | WO-2004084777 A2 | 10/2004 |

(56) References Cited

FOREIGN PATENT DOCUMENTS

| WO | WO-2005025466 |  | 3/2005 |
| WO | WO-2005048891 | A1 | 6/2005 |
| WO | WO-2006035014 | A2 | 4/2006 |
| WO | WO-2007128320 | A2 | 11/2007 |
| WO | WO-2008124716 | A2 | 10/2008 |
| WO | WO-2008124717 | A2 | 10/2008 |
| WO | WO-2009029610 | A1 | 3/2009 |
| WO | WO-2010060115 | A1 | 5/2010 |
| WO | WO-2010060116 | A1 | 5/2010 |
| WO | WO-2012061485 | A1 | 5/2012 |
| WO | WO-2015012953 | A1 | 1/2015 |

OTHER PUBLICATIONS

Chinese Patent Application No. 201510092347.8 Second Office Action dated Feb. 10, 2017.
European Patent Application No. 14829886.2 extended European Search Report dated Feb. 22, 2017.
EP07002257.9 Extended European Search Report dated May 16, 2007.
EP09828401.1 Extended European Search Report dated May 27, 2014.
EP11838737.2 Extended European Search Report dated Mar. 13, 2015.
PCT/US2009/066100 International Preliminary Report on Patentability dated May 24, 2011.
PCT/US2009/066100 International Search Report dated Feb. 12, 2010.
PCT/US2009/066100 Written Opinion dated Feb. 12, 2010.
PCT/US2009/066112 International Preliminary Report on Patentability dated May 24, 2011.
PCT/US2009/066112 International Search Report dated Mar. 12, 2010.
PCT/US2009/066112 Written Opinion dated Mar. 12, 2010.
PCT/US2011/058934 International Preliminary Report on Patentability dated May 7, 2013.
PCT/US2011/058934 International Search Report dated Feb. 10, 2012.
PCT/US2011/058934 Written Opinion dated Feb. 10, 2012.
PCT/US2014/039432 International Preliminary Report on Patentability dated Feb. 4, 2016.
PCT/US2014/039432 International Search Report dated Oct. 16, 2014.
PCT/US2014/039432 Written Opinion dated Oct. 16, 2014.
U.S. Appl. No. 13/123,920 Office Action dated Apr. 18, 2014.
U.S. Appl. No. 13/123,920 Office Action dated Apr. 29, 2013.
U.S. Appl. No. 13/123,920 Office Action dated Aug. 28, 2013.
U.S. Appl. No. 13/123,920 Office Action dated Dec. 12, 2014.
U.S. Appl. No. 13/123,920 Office Action dated Feb. 25, 2016.
U.S. Appl. No. 13/123,920 Office Action dated May 8, 2015.
U.S. Appl. No. 13/123,920 Office Action dated Sep. 11, 2015.
U.S. Appl. No. 13/123,920 Office Action dated Sep. 6, 2012.
U.S. Appl. No. 13/123,926 Office Action dated Apr. 17, 2013.
U.S. Appl. No. 13/123,926 Office Action dated Sep. 6, 2012.
Japanese Patent Application No. 2017-018452 Office Action dated Dec. 12, 2017.
U.S. Appl. No. 15/288,997 Office Action dated Nov. 2, 2017.
Australia Patent Application No. 2017208251 Examination Report No. 1 dated May 1, 2018.
Australian Patent Application No. 2014293635 Office Action dated May 4, 2018.
Chinese Patent Application No. 201480042044.9 Office Action dated Jun. 5, 2018.
Chinese Patent Application No. 201510092347.8 Office Action dated May 31, 2018.
European Patent Application No. 14829886.2 Office Action dated Mar. 9, 2018.
Indian Patent Application No. 3909/DELNP/2011 Office Action dated May 2, 2018.
Japanese Patent Application No. 2016-529761 Office Action dated Apr. 24, 2018.
U.S. Appl. No. 15/288,997 Office Action dated Jun. 8, 2017.
Chinese Patent Application No. 201510092347.8 Third Office Action dated Oct. 11, 2017 (No translation has been provided to date).
European Patent Application No. 09828400.3 extended European Search Report dated Oct. 20, 2017.
Chinese Patent Application No. 201510092347.8 Fourth Office Action dated Jan. 9, 2019.
Indian Patent Application No. 3908/DELNP/2011 Office Action dated May 25, 2018.
Japanese Patent Application No. 2016-629761 Decision of Refusal dated Feb. 25, 2019.
Brazilian Patent Application No. PI0920988-3 Pre-Examination Opinion dated Feb. 12, 2019.

* cited by examiner

A.

B.

C.

D.

E.

F

G.

A.

B.

C.

MOLDABLE ADHESIVE WAFERS

BACKGROUND OF THE INVENTION

The benefits of an ostomy wafer that can be molded to fit the size and shape of the stoma is known. See, e.g., U.S. Pat. No. 6,840,924. Such designs are suited for a two-piece ostomy wafer, to which is fitted an ostomy pouch by means of a removable coupling. Moldable ostomy wafer designs that can be used in conjunction with 1-piece ostomy pouch with an integral adhesive wafer are needed.

SUMMARY OF THE INVENTION

Disclosed herein are adhesive structures, more particularly moldable adhesive structures, used to seal a medical appliance, such as an ostomy appliance, to a subject's body about a body opening, such as a stoma.

In some embodiments, the moldable adhesive comprises at least two adhesive layers; and at least one layer of thin, flexible, elastic film between two adjacent adhesive layers to form a composite adhesive structure, wherein the moldable adhesive is formed by rolling or folding the composite adhesive structure onto itself such that the inner surface of the composite structure upon rolling provides a counteracting force to allow the edge of the rolled composite adhesive structure to partially return to its original size and shape.

In other embodiments, the moldable adhesives disclosed herein further comprise a wafer unit, wherein the moldable adhesive is attached to the wafer unit to form a molded surface of the wafer unit, wherein the molded surface of the wafer unit faces away from the body. In other embodiments, the molded surface of the wafer unit has a layer of film that extending partially across the surface, such that the inner opening of the film is larger than the inner opening of the surface. In yet other embodiments, the film layer is thin and flexible.

In some embodiments, the moldable adhesives disclosed herein provides an adhesive base of attachment for a faceplate of an ostomy pouch. In yet other embodiments, the faceplate is connected to the pouch as a separate element. In still other embodiments, the faceplate is adhesive.

In some embodiments, the moldable adhesives disclosed herein provide an outer edge of the composite structure, wherein the outer edge is larger than the opening in the pouch faceplate.

In other embodiments, the separate adhesive layers of the moldable adhesives disclosed herein comprise the same adhesive formulation. In still other embodiments, the separate adhesive layers comprise different adhesive formulations.

In some embodiments, the outer and inner edges of the composite structure are closed, non-intersecting geometric figures. In still other embodiments, the figures comprise a conic figure. In yet further embodiments, the figures are a circle. In other embodiments, the figures are a polygon.

Also disclosed herein are moldable medical devices and appliances. In some embodiments, the medical device or appliance is an ostomy appliance comprising a moldable ostomy wafer and an ostomy pouch, wherein the moldable ostomy wafer comprises a moldable adhesive. In some embodiments, the moldable adhesives which comprise the moldable ostomy wafer comprises at least two adhesive layers; and at least one layer of thin, flexible, elastic film between two adjacent adhesive layers to form a composite adhesive structure, wherein the moldable adhesive is formed by rolling or folding the composite adhesive structure onto itself such that the inner surface of the composite structure upon rolling provides a counteracting force to allow the edge of the rolled composite adhesive structure to partially return to its original size and shape.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3B depicts fitting of a subject's stomal opening size and shape to the moldable ostomy wafer. The moldable adhesive on the ostomy wafer is manipulated by rolling back the adhesive onto itself until the desired size and shape of the opening matches the subject's stoma (see FIG. 3C). Once fitted, a release liner on the proximal side of the moldable ostomy wafer is removed (FIG. 3D) and applied to the subject's skin surface around the stoma (FIGS. 3E-G). Pressure is applied throughout the distal surface of the ostomy wafer in order to ensure a good bond between the adhesive and skin surface.

FIG. 4A depicts removal of an exemplary release liner from the pouch wafer. Air is then allowed to enter the ostomy pouch by gently spreading the pouch as illustrated in FIG. 4B. The pouch is then applied to the moldable disc and skin (FIG. 4C). The task of placing the pouch onto the moldable disc and skin may be made easier by folding the pouch at the centerline prior to placement on the pouch wafer (FIG. 4C; left panel).

DETAILED DESCRIPTION OF THE INVENTION

Figure 1:
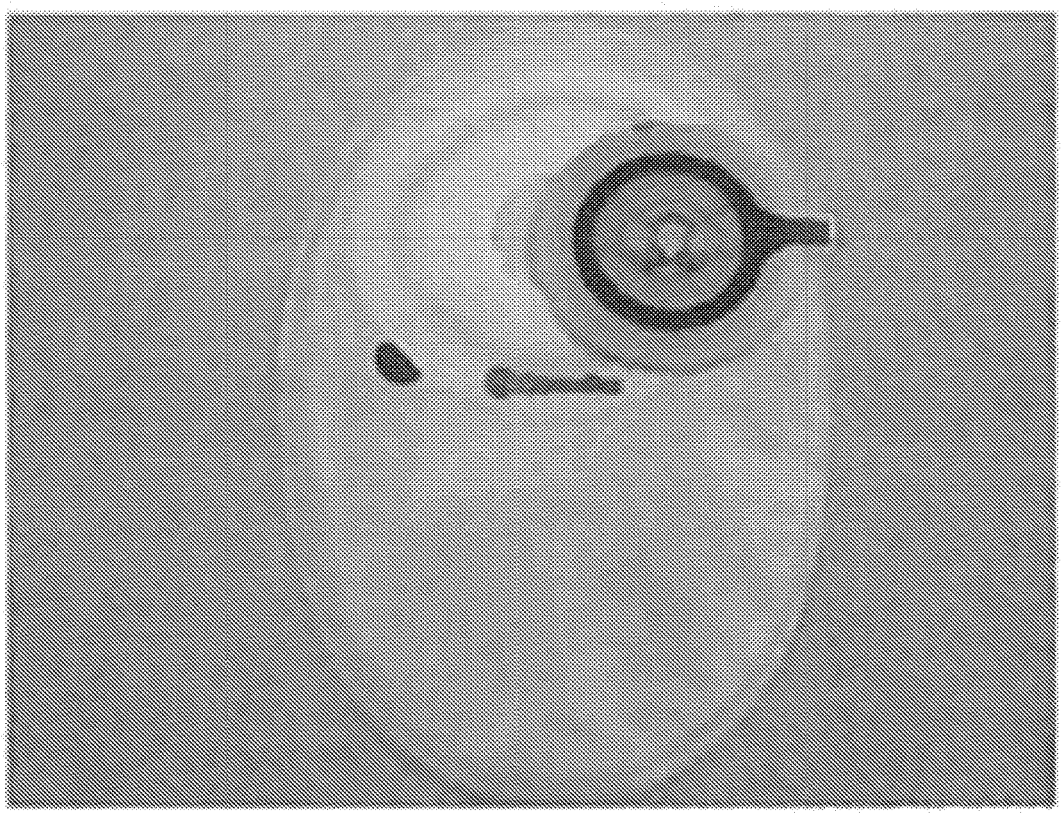
FIG. 1: Exemplary of a moldable ostomy wafer, which is removable and separate from an ostomy pouch.
Figure 2:
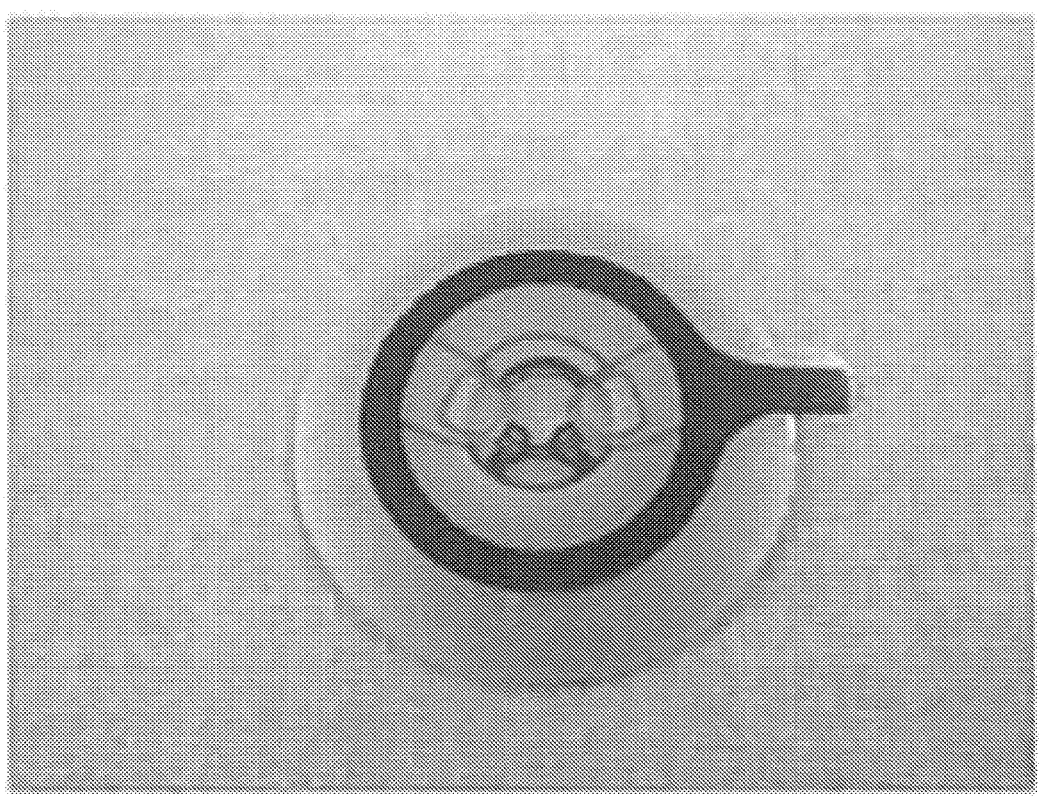
FIG. 2: Exemplary of a moldable ostomy wafer.
Figure 3:
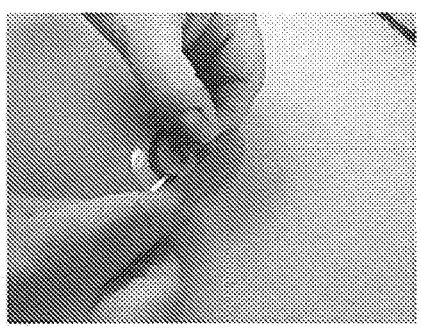
FIGS. 3A-G: Exemplary of a moldable ostomy wafer in operation. Prior to molding the ostomy wafer to a desired size to fit the stomal opening, a release liner covering the adhesive surface of the moldable ostomy wafer is removed (FIG. 3A).
Figure 3:
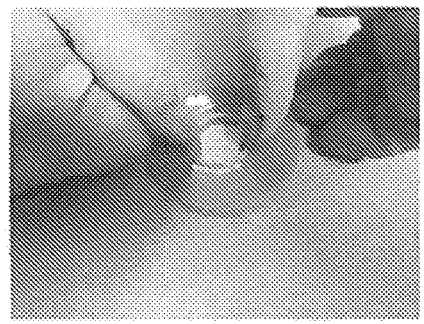
Figure 3:
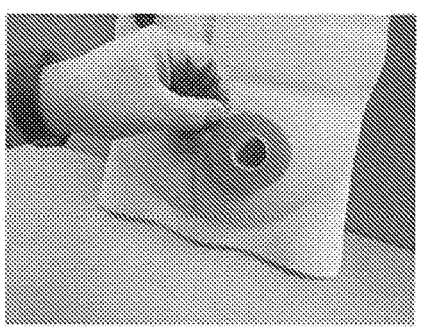
Figure 3:
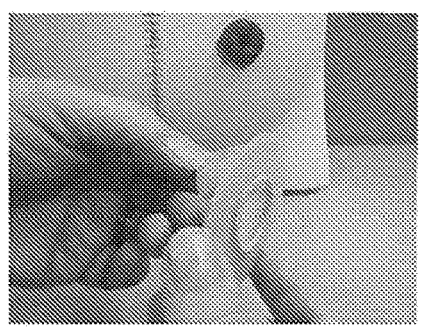
Figure 3:
Figure 3:
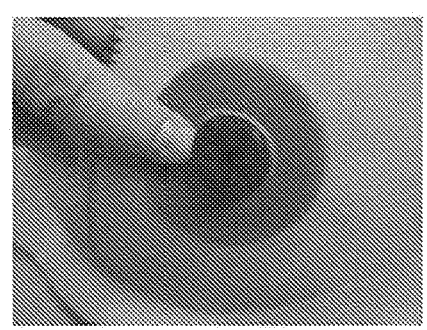
Figure 3:
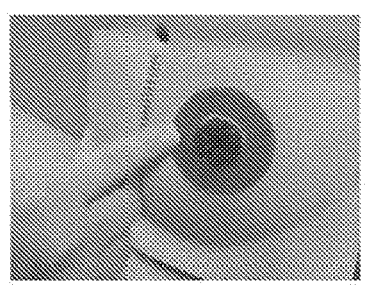
Figure 4:
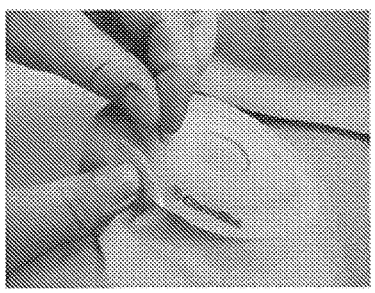
FIGS. 4A-C: Exemplary of an ostomy pouch in combination with the moldable ostomoy wafer.
Figure 4:
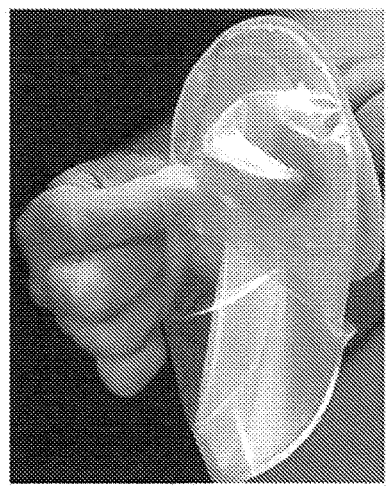
Figure 4:
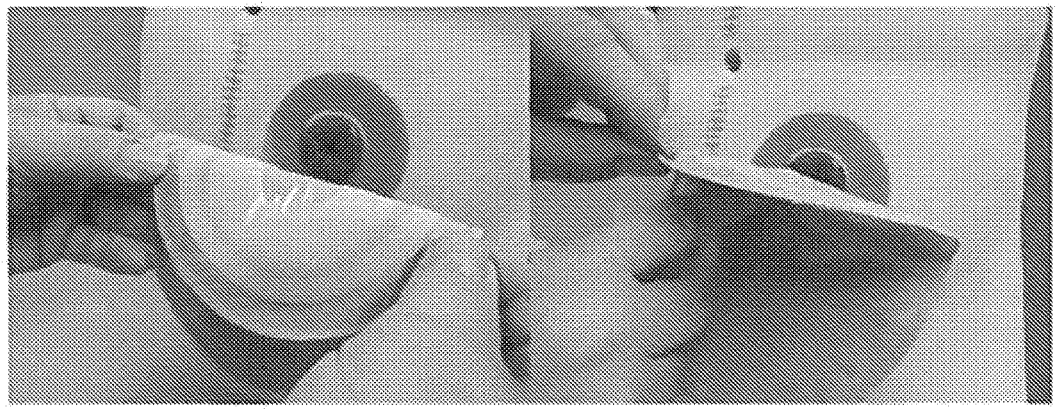

As used herein, the term "proximal" describes any surface contacting or facing the skin or the body. "Distal" describes any surface facing away from the skin or body.

Disclosed herein are methods and devices for coupling and securing a medical device or appliance. In particular, one piece moldable adhesive structures are disclosed which allow customization of an attachment wafer to the size and shape of, for example, a stoma, while allowing flexibility and security for attaching a medical device, such as an ostomy pouch or other device to the subject.

The disclosed embodiments are based on a ring of multilayer adhesive described in U.S. Pat. No. 6,840,924, which is incorporated by reference herein in its entirety. The adhesive of the moldable wafer, for example an ostomy wafer, features a multi-layer construction comprising separate layers of adhesive. The separate layers of adhesive may be different in formulation to one another, or may comprise the same formulation relative to each other. A flexible sheet with elastic properties is placed between at least two adjacent adhesive layers.

The composite structure comprising separate adhesive layers and at least one flexible sheet may be shaped by rolling an inner edge over itself. In the case of a ring made of such a composite, the inside diameter may be increased by this rolling motion. In such a rolling motion, one adhesive layer comes into contact with itself, and adheres to itself strongly enough to resist unrolling back to its original size. The inner layer of flexible, elastic film is pre-disposed to revert to its original configuration. This interaction of adhesive and restorative forces results in reducing the size of the molded opening in the ring. If the inside diameter of the composite structure ring is molded to a size slightly greater than the stoma, the interacting forces may cause the opening to close slight, which can create a close fit around the stoma. Such a close fit is desired as it provides sealing properties to resist leakage of effluent between the stoma and the composite structure.

It should be noted than in many cases the preferred direction of rolling, or molding the edge of the adhesive is to roll in onto the distal side of the structure. However, the embodiments described herein are not limited to this direction; instead, in some cases it may be desirable to roll the adhesive over the proximal adhesive surface in order to form a better seal and decrease the risk of leakage of effluent between the stoma and composite adhesive structure.

If the composite structure is formed in the shape of a planar, closed geometric shape, optionally with non-intersecting inner and outer edges, e.g circles and rings, the inner edge of such shapes can be adjusted to fit the size of a stoma by rolling, or molding the inner edge. While a ring a most desirable as a shape in conjunction with a moldable ostomy wafer structure, the inner and outer edges of the ring may be optionally constructed of symmetrical or asymmetrical polygons, or other desirable geometrical shapes.

The outer of the structure of the ring is formed to allow for the size of the ring to be sufficiently larger than the opening in the adhesive faceplate of an ostomy pouch. In turn, the opening in the pouch faceplate must be large enough to fit easily over the stoma itself without contacting the stoma. In one embodiment, the pouch adhesive faceplate may comprise a variety of openings to allow for such clearance in alternative circumstances, i.e., stomal size and shape differences. Likewise, the opening must not be too large so that the pouch adhesive does not contact the moldable adhesive ring when the ring and pouch are coupled together.

The surface of the ring may be fitted with a film component. The film would preferably be laminated to the surface of the ring, by means of the adhesive properties of the mating ring surface. The film would be made of a material that is resistant to effluent, is thin, flexible, and preferably non-elastic. Such a film component may include, for example, polyurethane, polyethylene or any material that is non-wettable and which adheres to the distal adhesive surface of the ring. Such a film component may also provide a consistent attachment surface for the pouch adhesive that attaches to it, and also allows for the wiping away of effluent that may be discharged from the stoma when the ring is fitted to the stoma. The inner edge of the film can also serve as a limit beyond which the inner edge of the molded ring preferably does not exceed.

In alternative embodiments, the ring may also be protected with layers of plastic film that are semi-flexible and non-elastic. Such structures may act to protect surfaces of the ring during molding and customization of the adhesive layer.

In use, the protective film would be removed from the surface of the ring to be molded. In a preferred embodiment, that surface is the distal surface. By gripping and rolling the inner edge of the exposed adhesive, the opening may be enlarged so that it exceeds the size of the stoma. The optional protective film may then be removed from the proximal surface of the ring. After attaching the ring to, for example a wafer unit, the inner edge of the ring may be finally adjusted inward to create a snug fit with the stoma.

In other embodiments, structures on the proximal surface of the moldable ostomy wafer may be molded. For example, after attachment of the ring to the stomal surface, the protective covering over an adhesive face of the pouch may be removed. The pouch adhesive may then be centered over the molded ring and attached to it. The bond between the pouch adhesive and the ring may have sufficient strength and integrity to form a single adhesive plate that is thin and flexible, in keeping with a 1-piece ostomy wafer, but further may also be easily molded to custom-fit a wide variety of stoma shapes and sizes.

In some embodiments, the ring and pouch may be packaged and sold as separate items. In other embodiments, the ring and pouch may be packaged in the same packaging container. In yet other embodiments, the ring may be directly attached a pouch in a packaging unit. In yet other embodiments, the ring may be mounted concentrically with the stoma opening in the pouch wafer, or alternatively may be offset in one or two axes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A moldable adhesive comprising:
   at least two adhesive layers; and
   at least one layer of thin, flexible, elastic film between two adjacent adhesive layers to form a composite adhesive structure;
   wherein a proximal surface of the moldable adhesive is attached to a distal surface of a wafer unit and the distal surface of the moldable adhesive faces away from a subject's body, wherein the moldable adhesive is capable of rolling or folding proximally towards the subject's body onto itself such that an inner surface of the composite adhesive structure formed upon rolling provides a counteracting force to allow an edge of the rolled composite adhesive structure to partially return to its original size and shape, and
   wherein a proximal surface of the wafer unit is configured to be attached to the subject's body.

2. The moldable adhesive of claim 1, wherein the molded surface of the wafer unit has a layer of film extending partially across the molded surface, such that an inner opening of the layer of film is larger than an inner opening of the molded surface.

3. The moldable adhesive of claim 2, wherein the layer of film is flexible.

4. The moldable adhesive of claim 2, wherein the moldable adhesive provides an adhesive base of attachment for a faceplate of an ostomy pouch.

5. The moldable adhesive of claim 4, wherein the faceplate is connected to the ostomy pouch as a separate element.

6. The moldable adhesive of claim 4, wherein the faceplate is adhesive.

7. The moldable adhesive of claim 4, wherein an outer edge of the composite adhesive structure is larger than an opening in the faceplate of the ostomy pouch.

8. The moldable adhesive of claim 1, wherein the two adjacent adhesive layers comprise the same adhesive formulation.

9. The moldable adhesive of claim 1, wherein the two adjacent adhesive layers comprise different adhesive formulations.

10. The moldable adhesive of claim 1, wherein outer and inner edges of the composite adhesive structure are closed, non-intersecting geometric figures.

11. The moldable adhesive of claim 10, wherein the closed, non-intersecting geometric figures comprise a conic figure.

12. The moldable adhesive of claim 10, wherein the closed, non-intersecting geometric figures comprise a circle.

13. The moldable adhesive of claim 10, wherein the closed, non-intersecting geometric figures comprise a polygon.

14. A moldable ostomy appliance comprising a moldable ostomy wafer and an ostomy pouch, wherein the moldable ostomy wafer comprises the moldable adhesive of claim 1.

15. The moldable adhesive of claim 10, wherein the proximal surface of the wafer unit is adhesive.

* * * * *